(12) United States Patent
Chanchani

(10) Patent No.: US 6,503,944 B1
(45) Date of Patent: Jan. 7, 2003

(54) ANHYDROUS SKIN CARE COMPOSITION

(75) Inventor: Niyati Chanchani, Cincinnati, OH (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 09/318,645

(22) Filed: May 26, 1999

(51) Int. Cl.[7] .......................... A61K 31/21; A61K 7/40; A61K 7/48; A61K 31/00; A61K 47/00

(52) U.S. Cl. .................. 514/506; 424/59; 424/78.02; 424/78.03; 424/401; 514/54; 514/63; 514/544; 514/724; 514/738; 514/762; 514/772; 514/772.3; 514/777; 514/785; 514/786; 514/787; 514/844; 514/847

(58) Field of Search .................. 424/401, 59, 70.1, 424/70.11, 70.12, 70.121, 70.13, 70.14, 70.31, 78.02, 78.03; 514/772, 772.1, 772.3, 785, 786, 787, 844, 845, 846, 847, 54, 63, 506, 544, 762, 724, 738, 777

(56) References Cited

U.S. PATENT DOCUMENTS

| | | | |
|---|---|---|---|
| 4,216,201 A | 8/1980 | Calvo | 424/63 |
| 4,291,018 A | 9/1981 | Oeda et al. | 424/64 |
| 4,814,165 A | 3/1989 | Berg et al. | 424/63 |
| 4,820,510 A | 4/1989 | Arraudeau et al. | 424/63 |
| 4,873,078 A | 10/1989 | Edmundson et al. | 424/64 |
| 4,919,934 A | 4/1990 | Deckner et al. | 424/401 |
| 4,944,937 A * | 7/1990 | McCall | 424/65 |
| 4,996,044 A | 2/1991 | Mercado et al. | 424/64 |
| 4,996,239 A | 2/1991 | Matravers | 424/64 |
| 5,039,518 A | 8/1991 | Barone et al. | 424/63 |
| 5,085,855 A * | 2/1992 | Shore | 424/64 |
| 5,093,111 A | 3/1992 | Baker et al. | 424/64 |
| 5,176,902 A | 1/1993 | Castro et al. | 424/63 |
| 5,225,186 A | 7/1993 | Castrogiovanni et al. | 424/64 |
| 5,288,482 A | 2/1994 | Krzysik | 424/64 |
| 5,292,530 A * | 3/1994 | McCrea et al. | 424/66 |
| 5,310,547 A | 5/1994 | Dunphy et al. | 424/64 |
| 5,447,715 A | 9/1995 | Roberts | 424/59 |
| 5,466,457 A | 11/1995 | Schneider et al. | 424/401 |
| 5,505,937 A | 4/1996 | Castrogiovanni et al. | 424/64 |
| 5,538,718 A | 7/1996 | Aul et al. | 424/64 |
| 5,593,662 A | 1/1997 | Deckner et al. | 424/64 |
| 5,645,842 A * | 7/1997 | Gruning et al. | 424/401 |
| 5,707,612 A | 1/1998 | Zofchak et al. | 424/69 |
| 5,744,146 A | 4/1998 | Peters et al. | 424/401 |
| 5,972,319 A * | 10/1999 | Linn et al. | 424/65 |

* cited by examiner

Primary Examiner—Allen J. Robinson
Assistant Examiner—Frank Choi
(74) Attorney, Agent, or Firm—Piper Rudnick LLP; Steven B. Kelber

(57) ABSTRACT

A new composition has been created which provide convenient solution for dry skin care needs. The composition is anhydrous and takes the form of a solid stick. The components of this product are:

5–50% of a wax;

10–80% of a hydrophobic liquid ingredient;

1–20% of a spreading agent; and optionally, 0–50% of a hydrophilic moisturizer.

14 Claims, 3 Drawing Sheets

ANHYDROUS SKIN CARE COMPOSITION

BACKGROUND OF THE INVENTION

1. Field of the Invention

The present invention relates to an anhydrous preparation for skin care applications, a method of applying an anhydrous skin care composition and a method of treating dry skin by applying an anhydrous skin care composition. It relates in particular to an anhydrous solid skin care composition.

2. Discussion of the Background

The skin care category consists of a broad array of products that treat dry skin. These products provide a wide range of perceived efficacies to the consumer, from "light" daily care products to therapeutic ointments and creams. The consumer selects a product from these categories, based on a self diagnosis of the severity of their dry skin symptoms. Generally, lotions are chosen to provide relief for symptoms at the lower end of the dryness scale, whereas creams and ointments are selected to treat symptoms of greater severity.

Dry skin problems of the greatest severity tend to be localized to small areas, such as hands, heels, elbows, etc. These parts of the body are consistently exposed to a harsh environment, for example, the hands are frequently washed with soap solutions and the elbows are repeatedly subjected to chafing and friction. Consequently, there is a propensity among consumers to use creams and ointments to treat these areas. There is one common complaint from consumers of these products, which is their perceived inherent greasiness. Creams and ointments are also messy to use, since to apply them, the consumer must either dip their hands in a jar or squeeze some product out on their fingers, and then rub the product on themselves. Due to these unappealing attributes, many consumers either use these products infrequently or completely avoid using them.

The primary goals of this invention are
1. to provide efficacious dry skin treatment,
2. that is not greasy,
3. in a convenient, easy to use form.

Matravers U.S. Pat. No. 4,996,239 reports a water resistant cream containing a synthetic wax of high molecular weight admixed with one or more hydrophobic silicones.

Edmundson et al. U.S. Pat. No. 4,873,078 reports a high-gloss, high-shine lipstick composition comprising isohexadecane in admixture with a lipstick formulation containing a heterogeneous mixture of at least two distinctly different colored dyes.

Deckner et al. U.S. Pat. No. 4,919,934 reports a wax based cosmetic stick comprising 10–50 wt. % of a wax and 5–90 wt. % of a poly α-olefin.

Baker et al. U.S. Pat. No. 5,093,111 reports a lipstick composition comprising waxes, oils, colorants, cetearyl isononanoate, sesquistearate and isopropyl hydroxystearate.

Castro et al. U.S. Pat. No. 5,176,902 reports a colored cosmetic stick comprising 1–99% natural wax, 0.001-about 20% of a colorant which is an aluminum salt and 0.001-about 20% of a $C_{12-60}$ fatty acid ester, in the absence of any $C_{12-60}$ fatty acid.

Krzysik U.S. Pat. No. 5,288,482 reports a lipcare cosmetic composition comprising an emollient, a suspending agent, a coloring agent, and an organosilicon compound.

Dunphy et al. U.S. Pat. No. 5,310,547 reports a colored cosmetic stick comprising 0.5 to about 25% water, 1 to about 99% of a solidifying agent and 0.001 to about 20% of a colorant which is an aluminum salt.

Castrogiovanni et al. U.S. Pat. No. 5,505,937 reports a cosmetic composition comprising 1–70% of a volatile solvent, 0.1–15% of a silicone resin, 10–45% of wax, 5–50% of powder and 1–30% of oil.

Roberts U.S. Pat. No. 5,447,715 reports a non-aqueous suncare composition comprising a volatile silicone oil and a conventional non-aqueous waterproof sunscreen formulation.

Deckner et al. U.S. Pat. No. 5,593,662 reports a moisturizing lipstick composition comprising a lipophilic material, a moisturizer, a colorant and a coupling agent.

Berg et al. U.S. Pat. No. 4,814,165 reports a solid hydrated stick product comprising 15–40% of a volatile cyclic silicone, 2–15% of oils, 2–20% of waxes, 2–7% of polyethylene glycol sorbitan beeswax, 10–40% of water and 0.1–40% of a cosmetically acceptable functional ingredient.

Mercado et al U.S. Pat. No. 4,996,044 reports a creamy soft lipstick formulation which is anhydrous comprising an anhydrous base intermediate, a color intermediate, an organic high staining dye, a dispersing oil of organic pigments, an acrylate copolymer intermediate, acrylate copolymer, and fragrance.

In spite of the variety of skin care compositions available commercially, there remains room for improvement, providing the desired attributes of 1) effective treatment of dry skin; 2) no greasy feel; and 3) a convenient and easy to use form.

SUMMARY OF THE INVENTION

The present invention is directed to an anhydrous skin care composition comprising:
  i) 5–50% of a wax;
  ii) 10–80% of a hydrophobic liquid ingredient;
  iii) 1–20% of a spreading agent; and
  iv) optionally, 0–50% of a hydrophilic moisturizing ingredient.

The present invention addresses the complaints arising from cream and ointment users: this product takes the form of a solid stick, provides efficacy equal to a cream or ointment application, which is convenient, and has appealing aesthetics. With this product, treatment can be applied directly to the localized area of damaged, severely dry skin, without using one's fingers. This product is anhydrous, and forms an occlusive barrier over the area of compromised skin. When this occlusive barrier is in place, the skin underneath it is shielded from further insult due to environmental factors, etc., and is given the opportunity to regenerate itself. The product is formulated to be non-greasy to the touch and quick absorbing, so that the perception of greasiness, stickiness and tackiness is eliminated.

The product is a combination of liquid and solid substances, which when melted together form a solid matrix, in which active ingredients are trapped. Hydrocarbon materials which are solid at room temperature and capable of forming crystalline matrices are preferably used to provide structure and rigidity to the stick. Hydrocarbon and silicone based liquid materials combine with the solids to reinforce the structure of the stick. Hydrophobic actives may be added to the stick by dissolving them into the stick base. Hydrophilic actives are stabilized in the stick by its physical structure.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
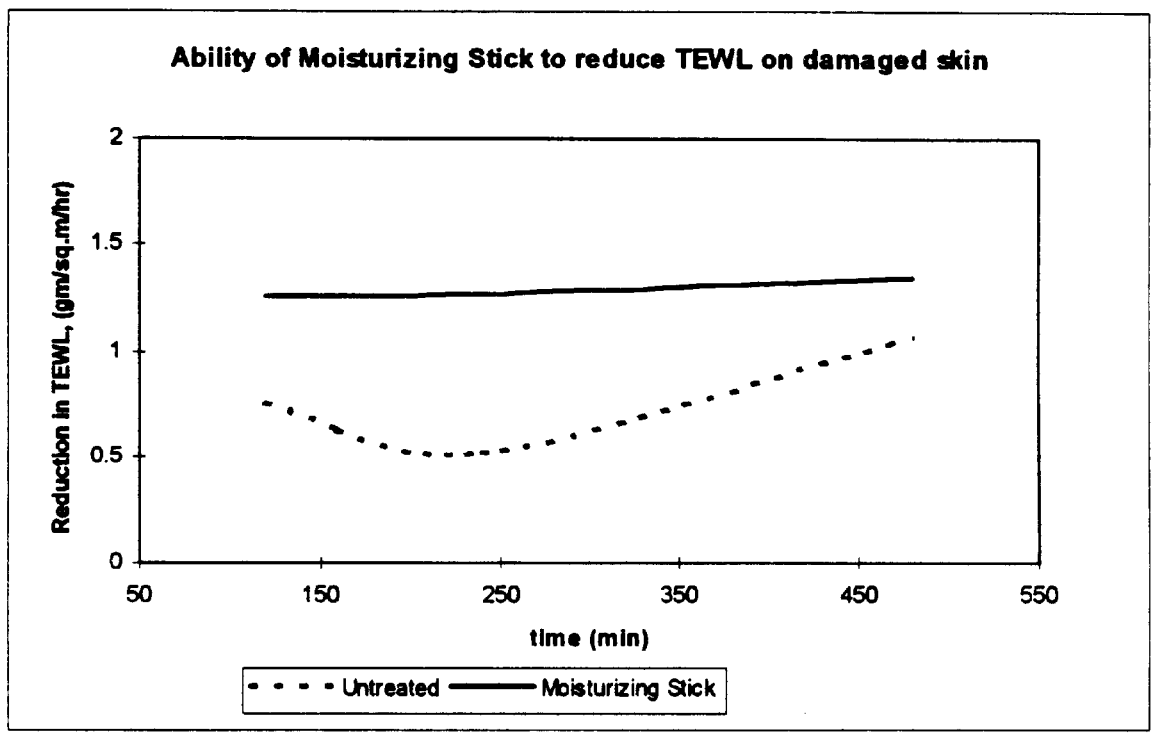
FIG. 1 illustrates transepidermal water loss measurements over time for treated and untreated skin.
Figure 2:
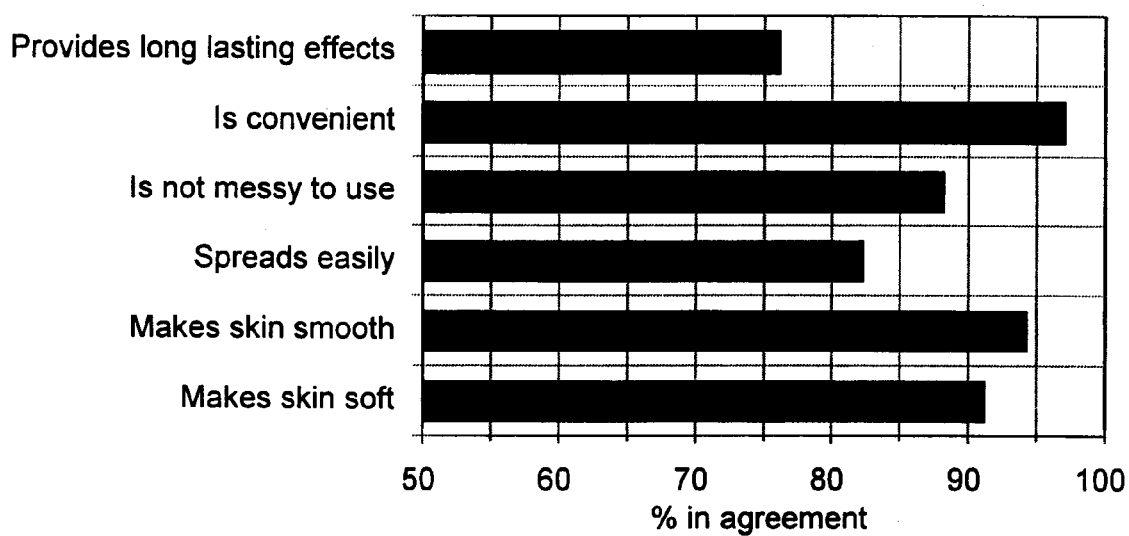
FIG. 2 is a graphical illustration of the results of the product testing in Example 6.

The present anhydrous skin care composition is comprised of 1) a wax component; 2) a hydrophobic liquid component; and 3) a spreading agent.

Wax component: These are a vital part of the formula since they form the crystalline structure which gives the stick rigidity and structure. In addition, the wax component is impenetrable to water and upon application forms a waterproof barrier to prevent escape of water through the skin. Since this moisturizing stick is used on body parts and applied with greater force than, for example, a lipstick, greater strength and rigidity is required from this product. The wax component is a solid at room temperature (25° C.) and will preferably have a melting point 40–100° C. Generally, the melting point will range from 60 to 80° C. Acceptable ingredients are all natural waxes, synthetic waxes (mono, di, and tri esters of saturated $C_{18}$–$C_{40}$ fatty acids with $C_{1-40}$ alcohols) and all waxes from petroleum sources. Also acceptable are ester and alcohol derivatives of straight and branched chain fatty acids that are solid at room temperature, for example cetyl and stearyl alcohol, glyceryl dilaurate, trihydroxystearin, etc. Specific materials include, hydrogenated castor oil (castor wax), synthetic waxes such as Fisher-Tropsch waxes, microcrystalline waxes, ethylene glycol diesters, triglyceride (preferably $C_{18-36}$) waxes, ethylene/vinylacetate copolymers, and mixtures thereof. Non-limiting examples include candelilla, beeswax, carnauba, spermaceti, montan, ozokerite, ceresin, paraffin, modified beeswax, bayberry, and mixtures thereof. However waxes from petroleum sources (ozokerite, ceresin, paraffin) are most preferable, since they have the greatest ability to form crystal structures in the presence of a high amount of liquid ingredients. The preparation of such materials is within the level of skill of those of ordinary skill in the art, for example as disclosed in U.S. Pat. No. 4,049,792.

The amount of wax component will be from 5–50 wt. % based on the total weight of the composition, preferably from 10–50 wt. %, more preferably from 20 to 35 wt. %.

Hydrophobic liquid Ingredients: The formula comprises one or more hydrophobic liquid ingredients. The hydrophobic liquid ingredient is liquid and free flowing at room temperature. It is non-volatile, that is, it does not have a measurable vapor pressure at room temperature. This ingredient serves as an emollient, and its primary function is to reduce the frictional and tactile characteristics of skin, i.e. make the skin feel soft and smooth. By nature it may or may not be occlusive or have an effect on the water content of skin. Together with the wax component, the hydrophobic liquid ingredient forms the bulk of the formula. The selection of this ingredient will determine the final greasiness and tackiness of the formula. Of choice are low viscosity (<2,000 cP) esters of straight and branched chain fatty alcohols and fatty acids for e.g. octyl isononanoate, di-isopropyl adipate, ethyl hexyl palmitate, isopropyl palmitate etc. Oils from vegetable sources are also acceptable, for e.g. castor oil, castor bean oil, sesame oil, sunflower oil, safflower oil, canola oil, peanut oil, rapeseed oil, soybean oil, palm kernel oil, etc. Hydrocarbons such as isohexadecane and USP light and heavy mineral oil are also acceptable The amount of liquid component will be from 10–80 wt. % based on the total weight of the composition, preferably from 20–70 wt. %, more preferably from 30 to 60 wt. %, and even more preferably from 40 to 50 wt. %.

Spreading agents: This ingredient promotes ease of spreading when the product is being rubbed on the skin. By allowing easy spreading, it eliminates the feeling of frictional drag and tackiness while the product is being applied. Suitable spreading agents will have a Skin Spreading Factor of from 2 to 14, preferably from 4–12, and more preferably about 8 when tested by the method described as follows:

$F_s=A_t/A_o$, where $F_s$=Skin Spreading Factor, $A_t$=spreading Area of Test Sample and $A_o$=Original Area 3.14 cm². A 2 cm diameter circle (3.14 cm² area) is defined on the volar forearm. 5 μl of the test sample are spread evenly within the area. After 15 min, the test area and surrounding forearm area are sprayed liberally with a 1.0% solution of FD&C Blue #1. The dye is allowed to remain for 30 seconds then rinsed off with warn water, patted dry, then examined for evidence of staining. The area not stained by the blue dye indicates areas of spreading of the spreading agent. The gross sectional diameter of the unstained area is measured in two directions and the average is used as the spread diameter. Non limiting examples of suitable spreading agents are polydimethylsiloxanes of viscosity <2,000 cP for e.g. dimethicone; alkyl modified polysiloxane copolymers for e.g. stearyl dimethicone; trimethyl phenyl silesquioxane for e.g. phenyl trimethicone. Certain mono and di esters of benzoic acid also exhibit appropriate spreading properties for this application, for e.g., dipropylene glycol dibenzoate.

The amount of spreading agent will be from 1–20 wt. % based on the total weight of the composition, preferably from 2–15 wt. %, and more preferably from 5 to 10 wt. %.

Moisturizing Ingredient: In order to further enhance the moisturizing effects of the anhydrous skin care composition, the composition may further comprise a moisturizer, typically hydrophilic in nature, which penetrates the skin and aids in its ability to retain water. Non-limiting examples include polyhydric alcohols, ethoxylated and propoxylated polyols, polysaccharides, glycerine, panthenol, hexylene glycol, polyethylene glycol, propylene glycol, sorbitol and mixtures thereof. Preferably the moisturizer is glycerin. Other examples include vitamins such as tocopheryl acetate, etc.; synthetic and natural ceramides such as cetyl-PG hydroxyethyl palmitamide, etc; urea; and allantoin.

The amount of hydrophilic moisturizing ingredient will be up to 50 wt. % based on the total weight of the composition, preferably from 10–50 wt. %, and more preferably from 20 to 35 wt. %.

Other optional ingredients: The preparation may in addition to the above ingredients contain additives, such as perfume; preservatives; inorganic powders such as talc and bismuth oxychloride, nylon, etc.; aluminum starch octenylsuccinate; sunscreen agents such as octyl methoxycinnamate, etc.; antihistamine ingredients such as histamine dihydrochloride, etc.; anti-itch ingredients such as hydrocortisone etc; analgesic actives such as methyl salicylate, etc. The amount and selection of perfume will be such that those of skill in the art will appreciate that the composition does not function as a deodorant composition, in terms of fragrance persistance.

The product form provides an excellent method to treat areas that are usually neglected, such as the heels, due to its unique form. The solid stick can be directly applied to the heels, or to the cuticles or knuckles, without getting any product on one's fingertips. Also, the product provides convenience in its natural portability, without the risk of spillage since the product is a solid.

This invention, due to its anhydrous nature, provides an ideal vehicle for the delivery of actives that cannot be delivered from traditional aqueous systems due to incompatibilities, for e.g., ascorbic acid.

Within the context of the present invention, the solid skin care composition is an anhydrous preparation, which will be understood by those of skill in the art, to mean that water has not been added as a component. However, those of skill in the art will also appreciate that water may be present in the composition via its presence in the formulation components and absorption from the atmosphere. In a preferred embodiment, the amount of water, if any, is $\leq 10$ wt. %, more preferably $\leq 5$ wt. %, even more preferably $\leq 2$ wt. %, even more preferably $\leq 1$ wt. %, and even more preferably $\leq 0.5$ w. %. The presence of water is disfavored, since it decreases the concentration of moisturizer.

The solid skin care composition according to the present invention typically will have an application surface area of $\geq 1$ cm$^2$, preferably $\geq 2$ cm$^2$, even more preferably $\geq 3$ cm$^2$, and even more preferably about 4–5 cm$^2$.

In a preferred embodiment, the solid skin care composition according to the present invention will not contain a sun screen agent, and will typically have a Sun protection factor (SPF) of $\leq 19$, preferably $\leq 15$, more preferably, $\leq 10$ and even more preferably $\leq 5$, even more preferably $\leq 4$, even more preferably $\leq 3$ and even more preferably $\leq 2$.

In another preferred embodiment, the solid skin care composition according to the present invention will not contain a pigment and or, colorant in an amount sufficient to impart a visibly detectable color change upon application. Accordingly, the solid skin care composition may comprise components which reflect and absorb wavelengths of light within the visible spectrum, (e.g $\lambda = 1.43–2.38 \times 10^4$ cm$^{-1}$), however, the total amount of such components is such that, upon typical application, there is no or only a slight, visibly detectable color change. Color change may be measured by using a Minolta chromameter, which provides color measurements in terms of red hues (a*), blue hues (b*), and brightness (L*) values. An application of this invention preferably does not alter L* by more than ±13 units, more preferably ±10 units, even more preferably ±8 units, and even more preferably ±5 units, and the a* or b* values by more than ±8 units, more preferably ±6 units, even more preferably ±4 units, and even more preferably ±2 units. Typically, a colored preparation intended for coloring and beautifying the skin will produce changes in L* values by more than ±15 units, and the a* or b* values by more than ±10 units.

In another preferred embodiment, the solid skin care composition according to the present invention will not contain an antiperspirant agent such as zirconyl hydroxychloride salts, aluminum chlorhydroxide salts, polyhydroxy complexes of basic aluminum salts, polyhydroxy derivatives of zinc and zirconium, complexes of basic aluminum halides or aluminum chlorhydrate, or a deodorant agent. Deodorant agents are characterized by a high fragrance durability, which provides an odor masking effect. The identification of a fragrance as a deodorant is clear to those of ordinary skill in the art.

The solid skin care composition according to the present invention may be prepared by conventional methods known to those of ordinary skill in the art, such as by melt blending in the optional presence of a solvent. By way of example, the wax ingredients(s) are weighed and heated to a temperature 10° F. greater than the drop point or flow point of the highest melting wax ingredient. While maintaining heating, the hydrophobic liquid ingredients and the spreading agents are added. The batch is then cooled to a temperature about 10° F. above the solidification temperature. At this point the hydrophilic moisturizing ingredients, if any are added, along with any other optional ingredients. After mixing, the batch is poured into suitable containers. The containers may be air cooled to room temperature, or may be passed through a cooling tunnel, wherein they may be cooled at a rate anywhere from 0.5 to 5° F./min.

The anhydrous solid skin care composition is preferably fabricated in the form of a stick and/or rod, having an exposed surface which may be used to apply the composition to skin. The stick and/or rod composition may be provided in a container equipped with a mechanism for exposing a greater portion of the exposed surface. A suitable container may be a hollow cylinder of circular or oval cross sectional shape, and may be made of a material such as polypropylene, high density polyethylene, or aluminum. The exposing mechanism may be as simple as having an open top and bottom ends to the container which would allow exposure of the exposed surface at the top end, by pushing at the bottom end. Exposure at the top end may also be achieved by a "screw" mechanism having an elevator cup on which the product rests, analogous to those used in lipstick containers, lip balm containers and deodorant containers. When the screw mechanism is turned, the elevator cup is raised or lowered, so that the product is raised or lowered above or below the rim of the cylinder.

A method of protecting skin from moisture loss, comprising applying the solid skin care composition as described above is another embodiment of the present invention. In a preferred embodiment, the composition is applied by rubbing an exposed surface of the solid composition onto skin. In one embodiment, the solid skin care composition is applied to skin other than the lips of the face.

While not wishing to be bound by any particular theory, the hypothetical mechanism of action of this product is as follows: when the product is applied to the skin, it forms an occlusive layer on the skin, which is impervious to the passage of water. This barrier 1) allows the underlying damaged skin to retain more moisture than usual, and 2) greatly reduces the insult caused by external environmental factors. Thus, the application of this occlusive barrier shields damaged skin and provides it with the opportunity to regenerate itself.

Having generally described this invention, a further understanding can be obtained by reference to certain specific examples which are provided herein for purposes of illustration only and are not intended to be limiting unless otherwise specified.

EXAMPLE 1

| Function | Component | Amount wt. % |
| --- | --- | --- |
| Wax Component | Ozokerite | 27 |
| | Carnauba | 3 |
| | Petrolatum | 2 |
| Hydrophobic Liquid | Isopropyl Myristate | 25 |
| | Corn Oil | 20 |
| Spreading Agent | Phenyltrimethicone | 5 |
| Moisturizing | Glycerine | 15 |
| Ingredient | Retinyl Palmitate | 1 |
| Optional Ingredients | Propyl Paraben | 0.5 |
| | Nylon | 1.3 |
| | Fragrance | 0.1 |
| | BHT | 0.1 |

The wax components were weighed in a suitable container and heated on a steam bath to a temperature of about 80° C. The liquid ingredients were added, followed by the spreading agent. The batch was cooled to about 50° C., and then the other ingredients were added, mixed for about 15 minutes, then poured into a suitable container.

EXAMPLE 2

| Function | Component | Amount wt. % |
|---|---|---|
| Wax Component | Candelilla | 3 |
| | Ceresin | 14 |
| | Behenyl Alcohol | 6 |
| | Petrolatum | 13 |
| Hydrophobic Liquid | Diisopropyl adipate | 8 |
| | Cetearyl Octanoate | 25 |
| | Mineral Oil | 12 |
| Spreading Agent | Stearyl Dimethicone | 2 |
| | Octyldodecyl benzoate | 8 |
| Moisturizing Ingredient | Sorbitol | 5 |
| | Cholesteryl Isostearate | 3.3 |
| Optional Ingredients | Propyl Paraben | 0.5 |
| | Fragrance | 0.1 |
| | BHT | 0.1 |

The wax components were weighed in a suitable container and heated on a steam bath to a temperature of about 75° C. The liquid ingredients were added, followed by the spreading agent. The batch was cooled to about 45° C., and then the other ingredients were added, mixed for about 15 minutes, and then poured into a suitable container.

EXAMPLE 3

| Function | Component | Amount wt. % |
|---|---|---|
| Wax Component | Candelilla | 5 |
| | Beeswax | 15 |
| | $C_{18-36}$ Acid Triglyceride | 8 |
| Hydrophobic Liquid | Octyl Perlargonate | 5 |
| | Soybean Oil | 20 |
| | Isopropyl Myristate | 10 |
| | Capric/Caprylic Triglyceride | 9 |
| Spreading Agent | Stearyl dimethicone | 2 |
| | Octyldodecyl benzoate | 5.3 |
| Moisturizing Ingredient | Glycerine | 13 |
| | Cholesteryl Isostearate | 5 |
| Optional Ingredients | Propyl Paraben | 0.5 |
| | Fragrance | 0.1 |
| | Talc | 25 |
| | BHT | 0.1 |

The wax components were weighed in a suitable container and heated on a steam bath to a temperature of about 80° C. The liquid ingredients were added, followed by the spreading agent. The batch was cooled to about 55° C., and then the other ingredients were added, mixed for about 15 minutes, and then poured into a suitable container.

EXAMPLE 4

| Function | Component | Amount wt. % |
|---|---|---|
| Wax Component | Ceresin | 3 |
| | Beeswax | 15 |
| | Petrolatum | 20 |
| Hydrophobic Liquid | Isostearyl Alcohol | 6 |
| | Corn Oil | 23 |
| | Cetyl Ricinoleate | 2 |
| | Cetearyl Octanoate | 12 |
| Spreading Agent | 2-Hexyl Ethyl Benzoate | 10 |
| Moisturizing Ingredient | Tocopheryl Acetae | 1 |
| | Ascorbyl Palmitate | 1 |
| Optional Ingredients | Propyl Paraben | 0.5 |
| | Fragrance | 0.1 |
| | Clover Oil | 0.3 |
| | Octyl Methoxycinnamate | 6 |
| | BHT | 0.1 |

The wax components were weighed in a suitable container and heated on a steam bath to a temperature of about 80° C. The liquid ingredients were added, followed by the spreading agent. The batch was cooled to about 55° C., and then the other ingredients were added, mixed for about 15 minutes, and then poured into a suitable container.

| Function | Component | A | B | C | D | E | F | G | H | I | J | K |
|---|---|---|---|---|---|---|---|---|---|---|---|---|
| Wax Component | Ceresin m.p.t ~65° C. | | 30.00 | | | 5.25 | 9.00 | | | 15.00 | 19.00 | 6.25 |
| | Ozokerite m.p.t ~70° C. | 22.25 | | 20.00 | 15.25 | 10.50 | 14.00 | 20.75 | | 11.00 | 4.00 | 15.50 |
| | Ozokerite m.p.t ~78° C. | | 10.5 | 20.00 | 15.25 | 10.50 | 6.75 | | | 4.75 | 9.75 | 7.50 |
| | Carnuba | 5.75 | 5.50 | | 15.50 | 5.50 | | 9.25 | | | | 4.50 |
| | Glyceryl Dilaurate | | | | | | 3.50 | | 9.50 | 2.50 | 5.50 | |
| | Beeswax | 3.00 | | | | | | | 15.50 | | | |
| | Petrolatum | 2.00 | | 3.75 | | | 13.50 | 8.00 | 15.50 | 13.50 | 13.50 | |
| Hydrophobic Liquid | Octyl Isononanoate | | | | | | 3.40 | | 10.20 | 5.20 | 2.70 | |
| | Isopropyl Palmitate | 20.00 | | 30.2 | | | 10.00 | 9.5 | | 8.00 | 9.00 | |
| | Corn Oil | 20.00 | 15.50 | | 20.7 | | | 21.50 | | | | |
| | Isopropyl Myristate | | 15.50 | | | | | | 25.00 | | | |
| | Mineral Oil light | q.s. | q.s. | q.s. | q.s. | q.s. | q.s. | q.s. | q.s. | q.s. | q.s | q.s. |
| | Cetearyl Octanoate | 15.00 | | | | 30.75 | | | | | | 21.75 |
| Spreading Agent | Cetyl Dimethicone | 5.00 | | | | | 2.00 | | 1.25 | 2.50 | 3.25 | |
| | C12–15 Alkyl Benzoate | | 5.00 | | | | 2.95 | 1.00 | 4.75 | 2.25 | 2.00 | |
| | Phenyltrimethicone | | | 5.00 | | | | 0.9 | | | | |
| | Stearyl Dimethicone | | | | 5.00 | | | 3.25 | | | | |

-continued

| Function | Component | Amount wt. % | | | | | | | | | | |
|---|---|---|---|---|---|---|---|---|---|---|---|---|
| | | A | B | C | D | E | F | G | H | I | J | K |
| Moisturizing Ingredient | 2-Hexyl Ethyl Benzoate | | | | | 5.00 | | | | | | 4.50 |
| | Tocopheryl Acetate | | | | | | 0.10 | | 0.20 | 0.25 | 0.05 | |
| | Cetyl PG Hydroxyethyl Palmitamide | | 1.00 | | | | 1.00 | | 1.25 | .95 | 1.50 | |
| | Sorbitol | 10.00 | | | | | | | | | | |
| | Cholesteryl Isostearate | | 3.95 | | | | | | | | | |
| | Ascorbyl Palmitate | | 5.25 | | | | 0.01 | | 0.05 | 0.20 | 0.10 | |
| Optional Ingredients | Propyl Paraben | 0.50 | 0.50 | | | 1.00 | | | | | | .80 |
| | Aluminum starch Octenylsuccinate | | | | | | 2.00 | | | 3.50 | 1.25 | |
| | Clover Oil | | | 0.10 | | | | | | | | |
| | Octyl Methoxycinnamate | | | | 0.20 | | | | | | | |
| | Nylon | | | | | | | | | | | |
| | Niacin | | | | | | 0.10 | | | 0.20 | 0.05 | |
| | BHT | 0.10 | 0.10 | 0.10 | 0.10 | 0.10 | 0.10 | 0.10 | 0.10 | 0.10 | 0.10 | 0.10 |
| | Fragrance | 0.10 | | 0.10 | | | | | 0.10 | | | |

EXAMPLE 6

Product Testing:

33 Females, ages 25–55, who suffer from dry skin trouble spots, and who presently use creams or lotions as treatment, were asked to try the moisturizing stick, as described below, at home over a period of 10 weeks. After the usage period they were asked to indicate agreement to a few statements.

The composition as tested is as follows:

| Component | function | wt. % |
|---|---|---|
| Ozokerite, m.pt ~65° C. | Wax Component | 10.00 |
| Ozokerite, m.pt ~70° C. | | 16.00 |
| Ozokerite, m.pt ~78° C. | | 6.75 |
| Glyceryl Dilaurate | | 6.60 |
| Isopropyl Palmitate | Hydrophobic Liquid | 17.80 |
| Octyl Isononanoate | | 3.40 |
| Mineral Oil, light | | 36.35 |
| Dimethicone | Spreading Agent | 2.00 |
| Propyl Paraben | Other | 0.80 |
| BHT | | 0.20 |
| Fragrance | | 0.10 |

The table below indicates their reply:

| Attribute | Number of responses (percent of total responses) | | | | | |
|---|---|---|---|---|---|---|
| | Makes skin soft | Makes Skin smooth | Spreads Easily | Is not messy to use | Is convenient | Provides long lasting effects |
| Agree Very Much | 16 (48) | 19 (58) | 18 (55) | 20 (61) | 24 (73) | 13 (39) |
| Agree Somewhat | 14 (42) | 12 (36) | 9 (27) | 9 (27) | 8 (24) | 12 (36) |
| Neither | 2 (6) | 1 (3) | 2 (6) | 1 (3) | 0 (0) | 4 (12) |
| Disagree Somewhat | 0 (0) | 0 (0) | 3 (9) | 2 (6) | 0 (0) | 3 (9) |
| Disagree Very Much | 1 (3) | 1 (3) | 1 (3) | 1 (3) | 1 (3) | 1 (3) |
| Total* | 33 (91) | 33 (94) | 33 (82) | 33 (88) | 33 (97) | 33 (76) |

*(% in agreement)

Clinical testing: Determining the effect of the moisturizing stick on the barrier function of the skin:

The barrier forming properties of the moisturizing stick were tested by applying a moisturizing stick as described below to damaged skin.

| | Wt. % |
|---|---|
| Wax Component | 46.75 |
| Hydrophobic Liquid | 45.08 |
| Spreading Agent | 4.95 |
| Moisturizing Ingredient | 1.11 |
| Other | 2.11 |

The forearm skin of human volunteers was damaged by applying sodium lauryl sulfate solution. The moisturizing stick product was then applied on the skin and Transepidermal Water Loss (TEWL) measurements were taken over time. TEWL is a measure of the rate of water loss through the skin and indicates the integrity of the skin as a barrier. Thus, greater reduction in TEWL indicates better barrier function. The results are illustrated in FIG. 1.

Another test of integrity is the ability of the barrier to prevent the penetration of external irritants. One such material is an organic dye, gentian violet, which shows remarkably rapid penetration into the skin. Its absorption into the skin can easily be measured by a Minolta Chromameter, which provides measurements in terms of red hues($a^*$), blue hues ($b^*$), and brightness ($L^*$) values. Dye penetration causes an increase in $b^*$ values.

Figure 3:
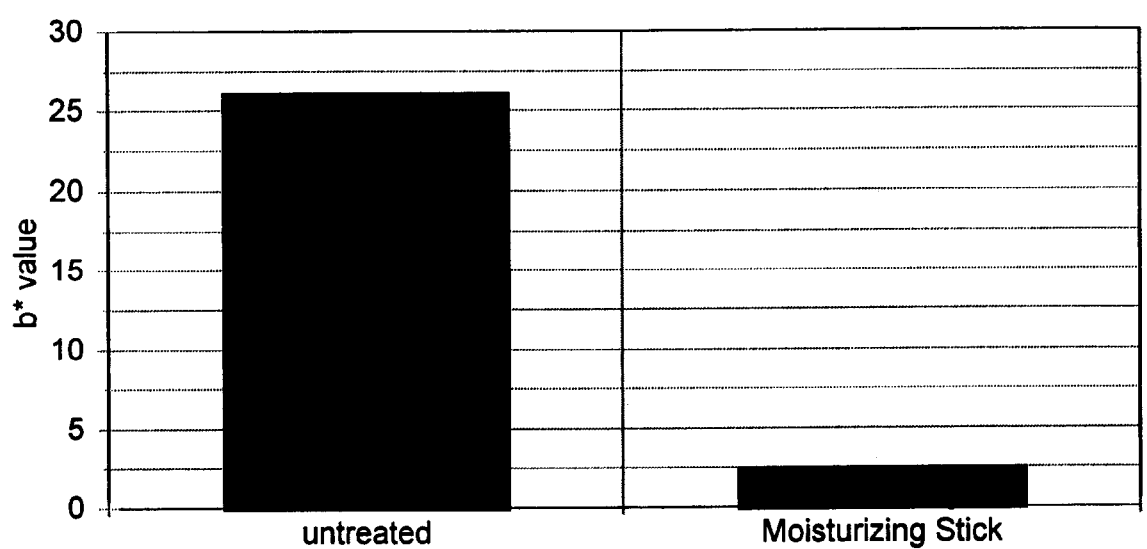
FIG. 3 is a graphical illustration of the b* valves on untreated skin versus skin treated with the moisturizing stick.

The color of two areas on the forearm skin on human volunteers was measured. Following this, one of the areas was treated with the moisturizing stick. The dye solution was applied next to both areas, and five minutes later the color measurements were retaken. As FIG. 3 shows, dye penetration shows a remarkable increase in the $b^*$ values on bare skin. Thus, an application of the moisturizing stick greatly reduces the penetration of the dye, showing its ability to reinforce the barrier function of the skin.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A solid composition comprising:
   i) greater than 20% and less than or equal to 50% by weight of a wax;
   ii) at least 10% by weight of a hydrophobic liquid;
   iii) 5–20% by weight of a spreading agent; and iv) a hydrophilic moisturizing ingredient;
    wherein said wax has a melting point of less than or equal to 100° C.;
    wherein said composition comprises ≦10 wt % water; and
    wherein said composition does not contain an antiperspirant agent.

2. The composition of claim 1, wherein said wax is selected from the group consisting of candelilla, beeswax, carnauba, spermaceti, montan, ozokerite, ceresin, paraffin, modified beeswax, bayberry, castor waxes, synthetic waxes, microcrystalline waxes, and mixtures thereof.

3. The composition of claim 1, wherein said hydrophobic liquid is selected from the group consisting of liquid esters of adipic acid, caprylic acid, captic acid, lauric acid, myrstic acid, palmitic acid, stearic acid, linoleic acid, linolenic acid, ricinoleic acid, oleic acid, elaidic acid, erucic acid, castor bean oil, castor oil, rapeseed oil, soybean oil, palm kernel oil, babassu kernel oil, coconut oil, and mixtures thereof.

4. The composition of claim 1, wherein said spreading agent comprises a polydimethylsiloxanes of viscosity <2,000 cPs.

5. The composition of claim 1, wherein said hydrophilic moisturizing ingredient is selected from the group consisting of polyhydric alcohols, ethoxylated and propoxylated polyols, polysaccharides, glycerine, panthenol, hexylene glycol, polyethylene glycol, propylene glycol, sorbitol and mixtures thereof.

6. The composition of claim 1, wherein said composition has an SPF of ≦19.

7. The composition of claim 1, wherein said composition does not alter L* by more than 13± units and a* or b* by more than ±8 units as measured using a Minolta chromameter;
    wherein L* is a measurement of brightness a* is color measurement in terms of red hues, and b* is color measurement in terms of blue hues.

8. The composition of claim 1, wherein said composition does not contain a deodorant agent.

9. The composition of claim 1, wherein said composition has an application surface area of ≧1 cm$^2$.

10. The composition of claim 1, wherein said composition does not contain a pigment or colorant in an amount sufficient to impart a visibly detectable color change upon application.

11. A method of preventing water loss from the skin, comprising applying the composition of claim 1 to skin.

12. The method of claim 11, wherein applying is by rubbing an exposed surface of said composition on said skin.

13. A solid composition comprising:
    i) greater than 20% and less than or equal to 50% by weight of a wax;
    ii) at least 10% by weight of a hydrophobic liquid; and
    iii) 5–20% by weight of a spreading agent selected from the group consisting of mono and diesters of benzoic acid;
    iv) a hydrophilic moisturizing ingredient;
        wherein said wax has a melting point of less than or equal to 100° C.;
        wherein said composition comprise ≦10 wt % water; and
        wherein said composition does not contain an antiperspirant agent.

14. A solid composition consisting essentially of:
    i) greater than 20% and less than or equal to 50% by weight of a wax;
    ii) at least 10% by weight of a hydrophobic liquid; and
    iii) 5–20% by weight of a spreading agent;
    iv) a hydrophilic moisturizing ingredient;
        wherein said wax has a melting point of less than or equal to 100° C.;
        wherein said composition comprise ≦10 wt % water; and
        wherein said composition does not contain an antiperspirant agent.

* * * * *